United States Patent
Mouchawar

(10) Patent No.: US 6,535,762 B1
(45) Date of Patent: Mar. 18, 2003

(54) COMBINATION ICD AND PACEMAKER SYSTEM HAVING INTEGRATED DISTAL ELECTRODE

(75) Inventor: Gabriel A. Mouchawar, Newhall, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/256,902

(22) Filed: Feb. 24, 1999

(51) Int. Cl.[7] ............................. A61N 1/362; A61N 1/39
(52) U.S. Cl. ............................................ 607/4; 607/122
(58) Field of Search ................................. 607/4, 116, 119, 607/121–123

(56) References Cited

U.S. PATENT DOCUMENTS

| | | | |
|---|---|---|---|
| 3,348,548 A | 10/1967 | Chardack | 128/418 |
| 3,769,984 A | 11/1973 | Muench | 128/404 |
| 4,325,389 A | 4/1982 | Gold | 128/784 |
| 4,592,372 A | 6/1986 | Beranek | 128/786 |
| 4,641,656 A * | 2/1987 | Smits | 607/5 |
| 4,848,352 A | 7/1989 | Pohndorf et al. | 128/642 |
| 5,080,097 A * | 1/1992 | Eisenberg | 607/2 |
| 5,097,843 A | 3/1992 | Soukop et al. | 128/784 |
| 5,181,526 A | 1/1993 | Yamasaki | 128/784 |
| 5,267,564 A | 12/1993 | Barcel et al. | 128/634 |
| 5,398,683 A | 3/1995 | Edwards et al. | 128/642 |
| 5,454,839 A * | 10/1995 | Anderson et al. | 607/123 |
| 5,470,342 A | 11/1995 | Mann et al. | 607/5 |
| 5,534,022 A * | 7/1996 | Hoffmann et al. | 607/122 |
| 5,571,157 A | 11/1996 | McConnell | 607/116 |
| 5,571,158 A | 11/1996 | Bolz et al. | 607/121 |
| 5,662,697 A * | 9/1997 | Li et al. | 607/122 |
| 5,913,887 A * | 6/1999 | Michel | 607/123 |

* cited by examiner

*Primary Examiner*—Kennedy Schaetzle

(57) ABSTRACT

The implantable cardiac stimulation system is adapted to transmit both shocking and pacing signals using a single electrode lead. The single biocompatible electrode, located at the distal end of the lead, includes a coil for shocking purposes and is in electrical continuity with an end cap which engages with the body tissue in a chamber of the patient's heart. The system delivers shocking, pacing and sensing signals between the single electrode and the enclosure for the ICD. Being of the same diameter as the electrical lead, the end cap preferably has a porous outer surface with an irregular relatively large surface area and an outer diameter substantially the same as that of the electrical lead.

4 Claims, 4 Drawing Sheets

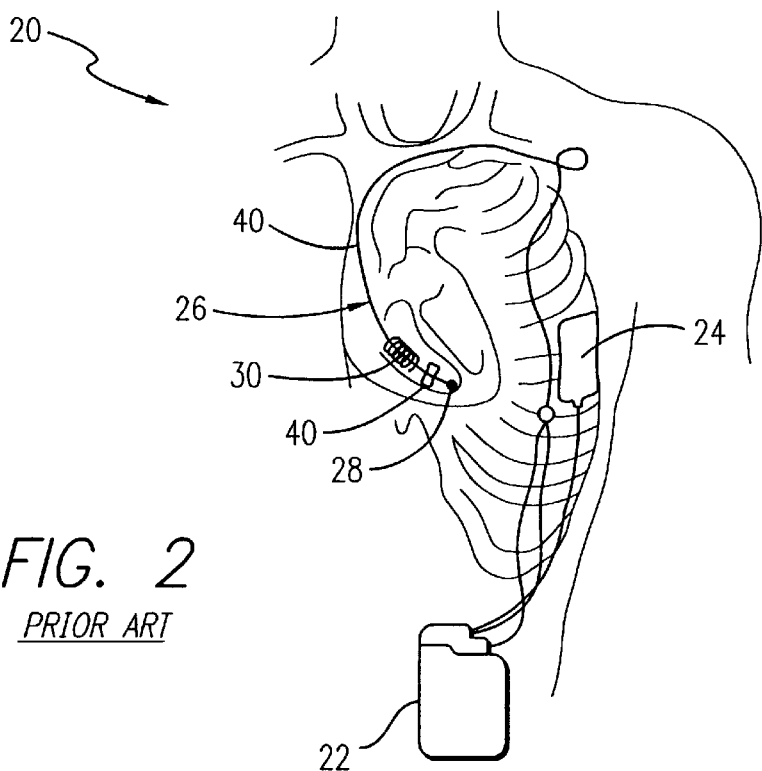
FIG. 2
PRIOR ART
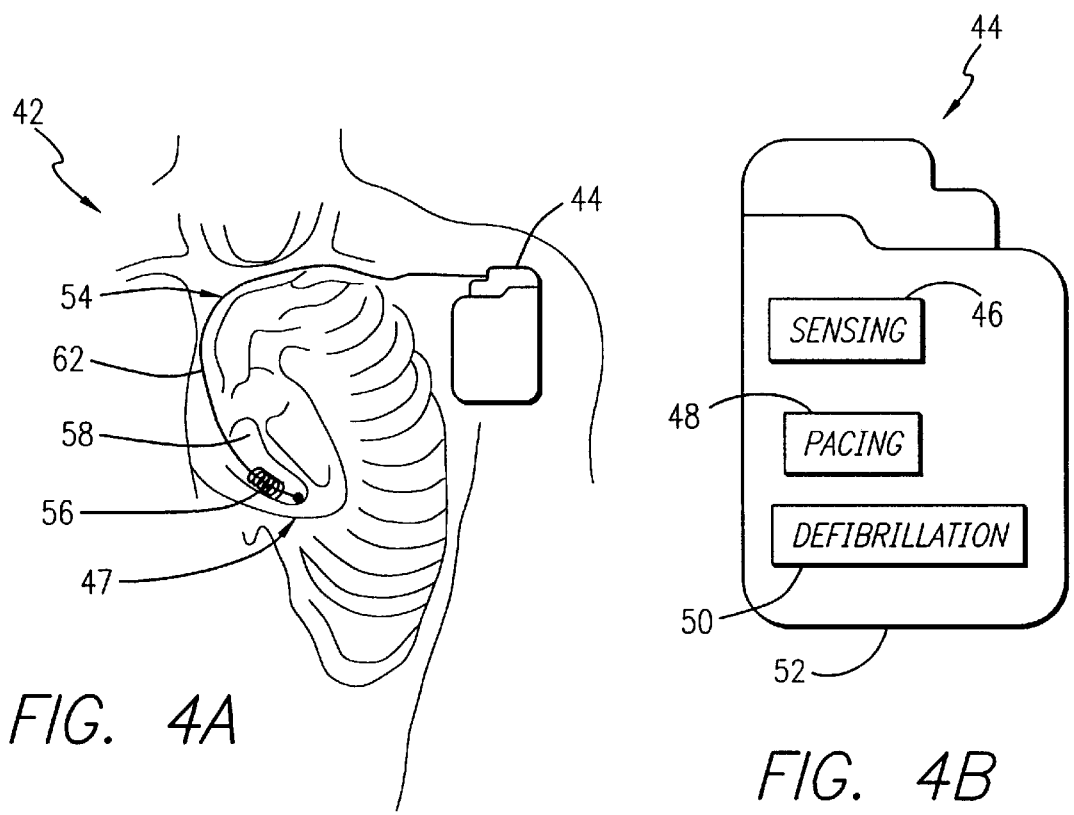
FIG. 4A
FIG. 4B

COMBINATION ICD AND PACEMAKER SYSTEM HAVING INTEGRATED DISTAL ELECTRODE

FIELD OF THE INVENTION

The present invention relates generally to implantable cardiac stimulation devices and, more particularly, to a simplified implantable lead for a combination implantable cardioverter/defibrillator (ICD) with bradycardia support pacing system adapted to transmit electrical signals using an improved distal end portion of the lead, the distal end performing shocking, pacing and sensing functions using a single electrode.

BACKGROUND OF THE INVENTION

A depolarization signal (a small electrical impulse) is generated by most muscle tissue as such tissue contracts. Thus, the beating or contracting of a human heart is manifest by appropriate depolarization signals evidencing: the contraction of the atria, referred to as the P-wave, and the contraction of the ventricles, referred to as the R-wave (or the QRS complex). The sequence of P-waves followed by R-waves thus comprises an electrogram or electrocardiogram signal that can be monitored by appropriate electrical circuits to indicate the status of the heart.

An implantable pacemaker includes sensing circuits that monitor the heart by looking for the occurrence of P-waves and/or R-waves, and pacing circuits that stimulate the heart with an appropriate electrical stimulation pulse in the event that a depolarization signal is not sensed within a prescribed time period. In this way, if the heart does not beat naturally within the prescribed time period, then an electrical stimulation pulse is provided to force the heart muscle tissue to contract, thereby assuring that the prescribed minimum heart rate is maintained.

An implantable cardioverter-defibrillator (ICD) typically includes sensing and pacing circuits to provide electrical stimulation pulses aimed at responding to slow intrinsic (natural) cardiac rates or asystole (a non-beating heart). The pacing circuits may also provide appropriate electrical stimulation pulses, typically in a prescribed burst or pattern, aimed at terminating rapid intrinsic rates (tachyarrhythmias or tachycardias).

With any bioelectric stimulation device, it is essential to determine accurately the ability of that device to accomplish the task for which it was designed. If nature were truly constant, and in-finitely small steps were used, theoretically it would be possible to define a limit, or threshold, below which no activation would occur and above which activation would occur 100% of the time (see FIG. 1A). In biological systems, such constancy is not possible. Instead, a balance point is the norm, at which activation occurs 50% of the time (E50 shown in FIG. 1B).

In addition, even with all external variables constant, there remains the inherent problem of biovariability, both subject-to-subject and time-dependent, thus yielding a sigmoidal-shaped curve (FIG. 1B) for finding the probability of success of a stimulus. For the investigator working with implantable defibrillators, variability is abundant, with some variables determinable, but most not, as they appear to vary either "randomly" or "chaotically." Despite major design improvements and mathematical expertise in the last two decades, our ability to understand the mechanisms of this variability has changed little since the classical experiments performed in the 1930s. Nevertheless, there have been several attempts to accurately assess defibrillation efficacy within a reasonable window of probability (also called the probability of success curve for defibrillation).

It is important to recognize that there is variation in the probability of any system to defibrillate at a particular instant in time (FIG. 1B). The spectrum of factors which may contribute to this variability are poorly understood. For example, the same setting on a defibrillator will fail on one attempt but be successful a few seconds later, with no obvious change in any measured variable.

There has been some suggestion that the mechanisms which alter efficacy due to the stochastic processes might be "random" or "chaotic". Although this has not been resolved, it seems implicitly clear that, as myocytes are not instantaneously depolarized and spontaneously repolarized, once a particular wave pattern of activation is established (at a given interval in time), in the next several milliseconds the pattern cannot be truly random since, to be truly random, all myocytes must have an equal chance of being reactivated. Clearly, those which are totally depolarized or are in the early phases of the activation will be in a refractory state and will not be reactivatable. Thus, for the subsequent several milliseconds, the movement of the wavefront(s) cannot be random. Therefore, although the tenant of randomness remains possible for the pattern in the first instant selected, a second selection within a short period of time thereafter cannot be random. Also, there may be some factors that influence defibrillation which are determinable.

The previous theory applies to atrial and ventricular defibrillation.

An ICD must perform at a minimum sensing, pacing, and defibrillation. Common ICDs use a multitude of electrodes to sense/pace and defibrillate. However the conventional approach, with dedicated electrodes for defibrillation, pacing, and sensing result in a complex, large lead body (greater than ~10 F). The large size of the lead results mainly because of insulation between the different conductors. In addition, due to the presence of a pacing dipole at the tip of a conventional lead, the defibrillation coil may be 2 cm away from the apical area when used in the right ventricle. This results in a low potential gradient near the apex and causes higher defibrillation thresholds.

Typical of the prior art in this regard, the following U.S. patents all disclose endocardial leads used for both sensing and pacing:

| Pat. No. | Inventor(s) | Issued |
|---|---|---|
| 5,571,157 | McConnell | Nov. 5, 1996 |
| 5,267,564 | Barcel et al. | Dec. 7, 1993 |
| 4,848,352 | Pohndorf et al. | July 18, 1989 |
| 4,592,372 | Beranek | June 3, 1986 |

Each of the following U.S. patents discloses an electrode assembly for an implantable lead:

| Pat. No. | Inventor(s) | Issued |
|---|---|---|
| 5,571,158 | Bolz et al. | Nov. 5, 1996 |
| 5,181,526 | Yamasaki | Jan. 26, 1993 |
| 5,097,843 | Soukop et al. | Mar. 24, 1992 |
| 4,325,389 | Gold | Apr. 20, 1982 | and the patents to Soukop et al., Yamasaki, and Bolz et al. specifically disclose porous electrode constructions for increasing the effective surface area of the electrode. It was with knowledge of the foregoing state of the technology that the present invention has been conceived and is now reduced to practice.

SUMMARY OF THE INVENTION

The present invention relates to an implantable stimulation system and lead which is adapted to transmit electrical signals between a return electrode and an "integrated" distal electrode capable of providing pacing pulses and shocking pulses, as needed, to stimulate selected body tissue, in addition to receiving cardiac signals. Whereas the prior art required separate electrodes for pacing/sensing, shocking, the present invention advantageously integrates all these functions into a single electrode, significantly simplifying the lead's construction.

Although the previous background material is directed towards ventricular defibrillation, the same principles of the invention can be applied to atrial defibrillation.

The present invention is compatible with an implantable cardioverter defibrillation (ICD) device, which includes circuitry for sensing intrinsic depolarization signals of the patient's heart, first and second stimulating circuitry for generating electrical pacing pulses and defibrillation pulses, respectively, and transmitting such pulses to the patient's heart, and an electrically conductive enclosure (i.e., the housing or "case" electrode) protectively supporting and encompassing the sensing circuitry, and the first and second stimulating circuitry.

The present invention is directed towards an improved implantable lead having a single biocompatible electrode at the distal end of the lead which engages with the body tissue in the right ventricle of the patient's heart. The implantable lead connects the electrode to the ICD for transmitting the sensing, pacing, and defibrillation pulses, respectively.

The distal electrode includes an end cap in electrical continuity with the lead, the end cap having a diameter in the range of about 1–3 mm and a length in the range of about 2–10 mm. Being of the same diameter as the electrical lead, the end cap preferably has a porous outer surface with an irregular relatively large surface area and an outer diameter substantially the same as that of the electrical lead. The distal electrode further includes a coil in electrical continuity with the end cap, the coil having a length suitable for placement in the ventricle, typically about 2–10 cm.

In short, a simple defibrillation/sense/pace electrode system is being proposed by the invention. A single coil electrode with an end cap is to be placed in the right ventricle and a platinized (or titanium nitride coated) end cap incorporated into the system to help increase the surface area of the tip. The case electrode for the ICD is the only other electrode in this first embodiment. Pacing and sensing is done between the coil and the device's enclosure similar to a unipolar pacemaker. Defibrillation is done between the coil and the ICD's enclosure.

In a second embodiment, a second coil electrode may be placed in the superior vena cava (SVC), which may act as the return electrode in lieu of the case electrode described above. In this embodiment, the lead requires only two conductors.

A primary feature, then, of the present invention is the provision of a simplified lead for an implantable cardioverter/defibrillator (ICD) adapted to transmit electrical signals between a proximal end portion of the lead and a distal end portion of the lead and to thereby stimulate selected body tissue.

Another feature of the present invention is the provision of such a simplified lead according to which a single coil electrode with an end cap is placed in the right ventricle, the enclosure for the ICD being the only other electrode for the system.

Still another feature of the present invention is the provision of such a simplified lead which utilizes a platinized or titanium nitride coated or otherwise coated end cap for increasing the effective surface area of the tip portion.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 2 is a diagrammatic illustration of the installation of a conventional medical system, specifically, an ICD and associated components, in the upper chest region of a human being;

FIG. 4 is a diagrammatic illustration of the installation of a medical system embodying the present invention, specifically, an ICD and associated components, in the upper chest region of a human being;

FIG. 4A is a generalized block diagram of the main components of an ICD;

DETAILED DESCRIPTION OF THE PREFERRED EMBODIMENTS

Figure 1A:
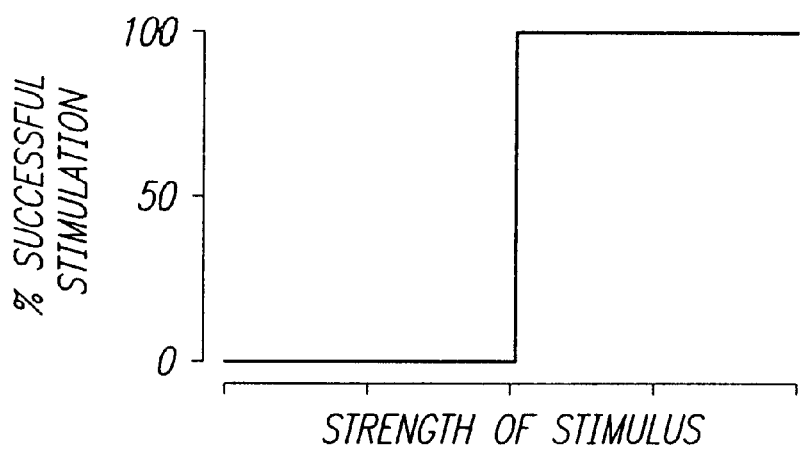
FIGS. 1A and 1B are graphs presenting generalized figures of biological responses related to a range of stimulation intensities, FIG. 1A indicating the response with a virtual threshold, FIG. 1B indicating the sigmoid response.
Figure 1B:
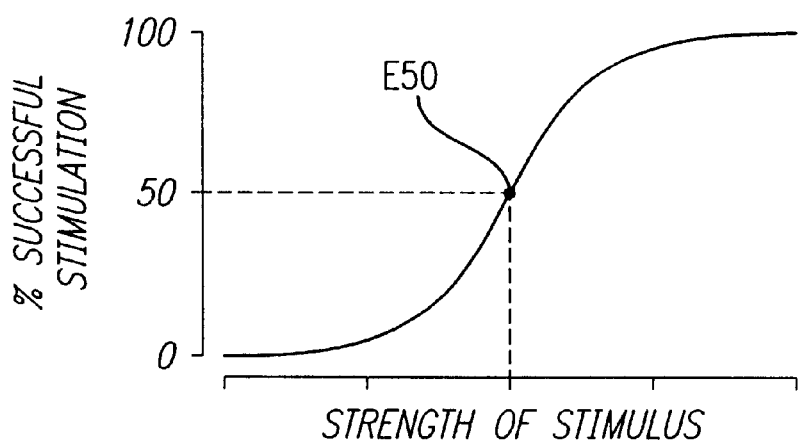

FIGS. 1A and 1B are merely graphs presenting generalized figures of biological responses related to a range of stimulation intensities, and have already been discussed above in conjunction with the Background.

Figure 3:
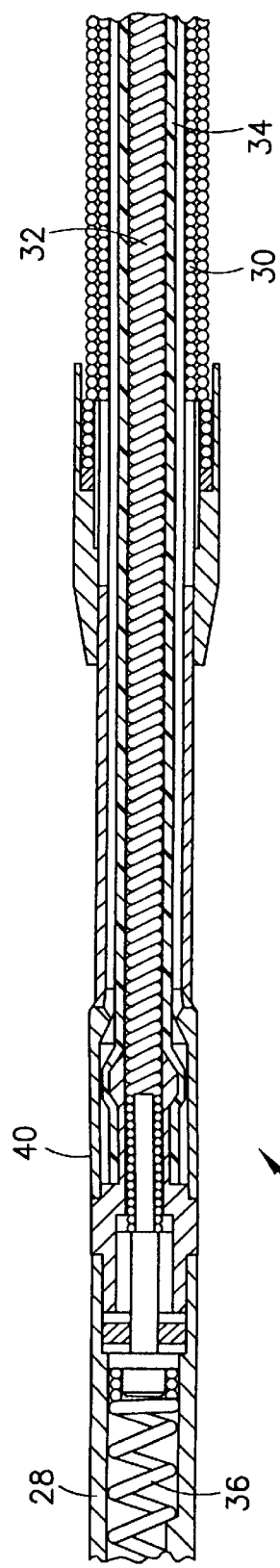
FIG. 3 is a side elevational view, in section, of a conventional endocardial lead at a pacing distal end.

Turning now to FIGS. 2 and 3, there is generally illustrated the configuration of a known prior art implantable medical system 20 for use with an implantable cardioverter/defibrillator (ICD) 22.

In the customary fashion, the medical system 20 utilizes a subcutaneous patch electrode 24 and an endocardial lead 26 terminating at a pacing tip portion 28. The lead 26 incorporates a defibrillation coil 30 and a pacing/sensing conductor 32 separated by suitable electrical insulation 34. The pace/sense tip electrode 36 may be an active screw-in fixation type electrode. The endocardial lead 26 also includes a sense/pace ring-type electrode 40. It was earlier explained that the lead system 20 utilizes a complex, large lead body (greater than ~10 F), the large size being mainly due to the insulation 34 between the different conductors, specifically, the defibrillation coil 30 and the pacing/sensing conductor 32 and insulation between the tip electrode 36 and ring 40 of the pace/sense electrodes.

Figure 5:
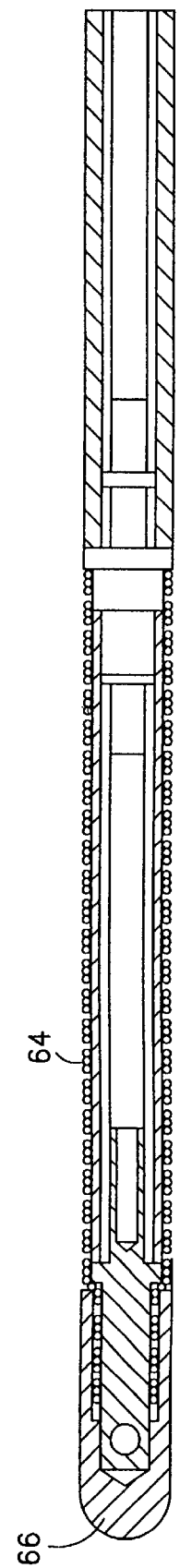
FIG. 5 is a side elevational view, in section, of a new endocardial lead terminating at a pacing distal end as used in the medical system illustrated in FIG. 4.

In keeping with the invention, FIGS. 4A, 4B and 5 show an improved body implantable medical system 42 which includes an ICD device 44 including sensing circuitry 46 for sensing intrinsic depolarization signals of the patient's heart, first stimulation circuitry 48 for generating electrical pacing pulses and transmitting such pulses to the patient's heart 47, second stimulation circuitry 50 for generating electrical defibrillation pulses and transmitting such pulses to the patient's heart, and an electrically conductive enclosure 52 protectively supporting and encompassing the sensing circuitry 46 and the stimulation circuitry 48, 50.

A lead 54 associated with the ICD 44 terminates at its distal end at a single electrode 56 which is adapted for placement in the right ventricle 58 of the patient's heart 47 for engagement with the body tissue of the heart. The lead 54 includes an lead body 62 which contains a single electrical conductor (not shown) which connects the coil electrode 56 to the ICD 44.

As shown in more detail in FIG. 5, the electrode 56 is composed of a biocompatible material and includes a single coil electrode 64 and an end cap 66 which is in electrical continuity with the lead 62. The end cap 66 preferably has a diameter in the range of about 1 mm to about 3 mm and a length of 2–10 mm. The coil electrode 64 has a length suitable for placement in the ventricle, e.g., in the range of about 2 cm to about 10 cm.

The end cap 66 has an outer diameter substantially the same as the outer diameter of the electrical lead 62 and an outer surface.

The end cap may employ a plurality of electrically conductive globules joined together to form a porous mass thereby defining a plurality of pores throughout the porous mass such that the outer surface has an irregular, relatively large surface area to enhance passive fixation.

The outer surface may be platinized or titanium nitride coated, for example, generally in the manner disclosed in commonly assigned U.S. Pat. No. 5,097,843 to Soukup et al. In this manner, the end cap helps to significantly increase the effective surface area of the electrode 56.

Other methods of actively or passively fixating the distal end may also be employed and are well known to those of skill in the art, and are considered within the spirit of the invention.

In a first embodiment, the enclosure 52 of the ICD 44 can be the only other electrode used in the system 42. Advantageously, the lead can be a single conductor lead, which significantly reduces the diameter of the lead and its complexity to manufacture.

In a second embodiment, the lead can contain another defibrillation coil located in the superior vena cava (SVC), making the lead a little larger but giving the flexibility to defibrillate by delivering the current from RV coil to both the SVC electrode and ICD enclosure simultaneously. Pacing and sensing is performed between the coil and the device's enclosure similar to a unipolar pacemaker. Defibrillation is also performed between the coil and the ICD's enclosure.

Animal Experiment Using New Lead

Figure 6:
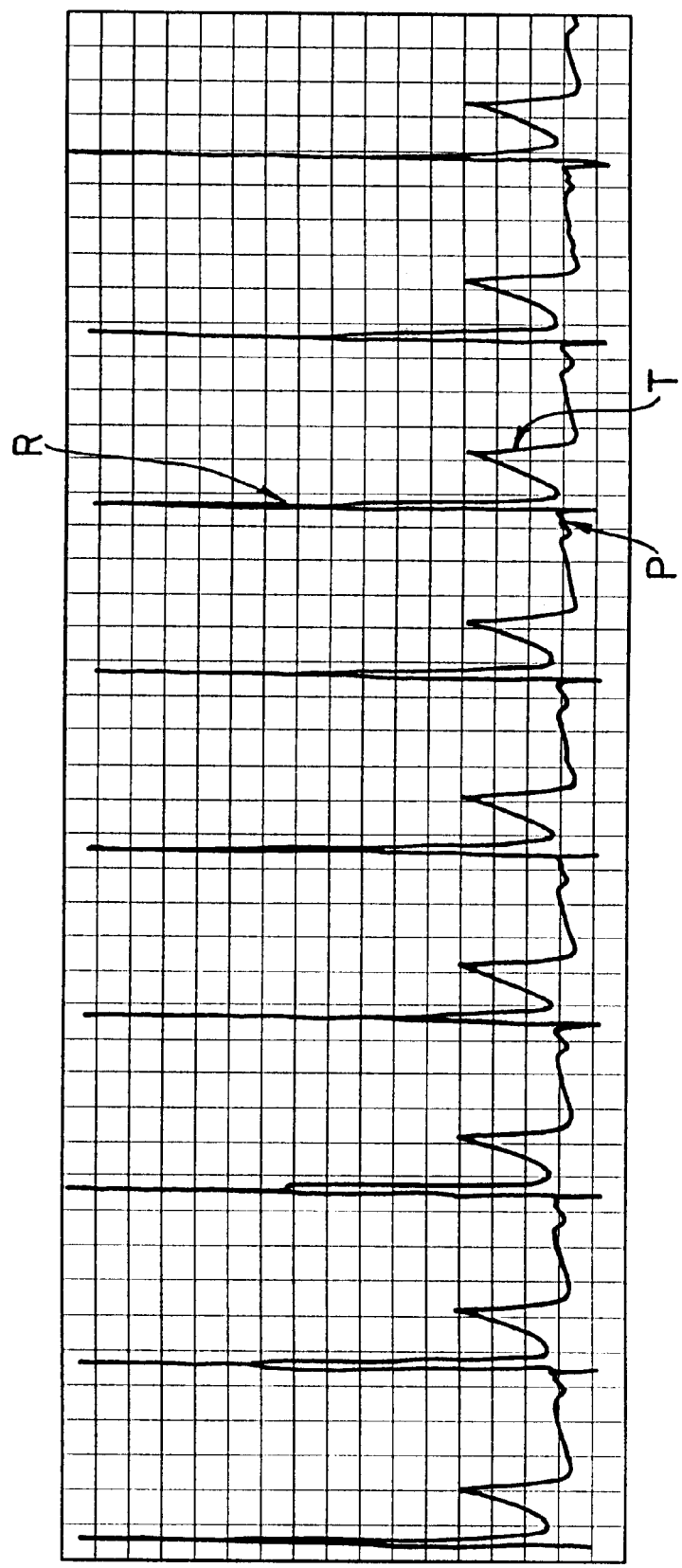
FIG. 6 is an electrocardiogram recorded between the electrode of the invention and the ICD enclosure according to the installation of the medical system illustrated in FIG. 4.

The applicant constructed the lead 56 and conducted an animal experiment using the medical system 42 on Oct. 18, 1994 to verify its performance. The electrogram illustrated in FIG. 6 was recorded (band limited to 0.3–300 Hz) between the electrode 56 and the enclosure 52 of the ICD 44. Clearly visible are the R- and T-waves. A small amplitude P-wave can also be seen. For purposes of this invention, the use of this signal is proposed for sensing the intrinsic cardiac rate which is processed by the circuitry in the ICD. The pacing threshold for capture of this lead was measured to be 4.1 V at a pulse duration of 0.5 ms, with a 150 ohm pacing lead impedance, when the pacing pulses were applied between the electrode 56 and ICD housing 44.

Animal Experiment Using Conventional Lead

The defibrillation performance of the lead 54 was then compared to that of a conventional lead, such as lead 26 (FIGS. 2 and 3). This animal had higher than average DFT (defibrillation threshold) for dogs with his body weight. With the conventional lead system (RV→SVC&SQ) as seen in FIG. 2, DFT, consistent defibrillation (DFT+) and E50 (FIG. 1B) were 36 J, 36 J and 32.7 J, respectively.

When the conventional RV lead 26 was replaced with the new lead 54 of the invention, the thresholds were reduced to 12 J, 14 J and 9.3 J corresponding to DFT, DFT+ and E50, respectively. In addition, no visible myocardial damage was seen despite delivering 86 shocks from the electrode 56. To summarize the results of this experiment, it was found that the new lead 56 reduces DFTs by more than 50%. This is attributed to the ability to reach closer to the RV apex with the defibrillation coil. Sensing and pacing are also possible between the new lead and the enclosure of the ICD.

Thus, a simple lead system has been described with one coil electrode in the heart and the other electrode being the enclosure of the ICD. The associated ICD which contains a single unipolar feedthrough greatly simplifies its header. The size of this coil electrode could be less than 8 F. Its defibrillation performance surpasses that of current leads. The tradeoff is that its pacing threshold was 5 to 8 times higher than conventional pacing leads. However, since the primary ICD-using patient doesn't need long periods of bradycardia support, its other benefits outweigh this cost.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable cardiac stimulation system, comprising:
    an implantable cardioverter defibrillation (ICD) device including sensing means for sensing cardiac signals of a patient's heart, first pulse generating means for generating pacing pulses in the absence of cardiac signals, second pulse generating means for generating shocking pulses to the patient's heart in response to abnormal cardiac signals, and an electrically conductive enclosure acting as a return electrode; and
    an implantable lead having a single electrode located at the distal end of the lead for contact with the body tissue, the electrode being adapted for delivering the shocking pulses and the pacing pulses and for receiving the cardiac signals therethrough.

2. The implantable cardiac stimulation system as set forth in claim 1, wherein the electrode comprises:
    a single coil electrode; and
    an end cap in electrical continuity with the single coil electrode, the end cap being adapted for contact with the apex of the ventricle.

3. The implantable cardiac stimulation system as set forth in claim 2, wherein:
    the end cap has an outer surface including a plurality of electrically conductive globules joined together to form a porous mass thereby defining a plurality of pores throughout the porous mass,
    whereby the outer surface has an irregular relatively large surface area.

4. The implantable cardiac stimulation system as set forth in claim 2, wherein the end cap has an outer diameter substantially the same as the outer diameter of the electrical lead.

* * * * *